(12) United States Patent
Lipkowski et al.

(10) Patent No.: US 9,486,493 B2
(45) Date of Patent: Nov. 8, 2016

(54) USE OF A PEPTIDE AND AN ANALGESIC PHARMACEUTICAL AGENT

(76) Inventors: Andrzej W. Lipkowski, Warsaw (PL); Daniel Carr, Chestnut Hill, MA (US); Aleksandra Misicka-Kesik, Piastow (PL); Piotr Kosson, Warsaw (PL); Anna Klinowiecka, Warsaw (PL)

( * ) Notice: Subject to any disclaimer, the term of this patent is extended or adjusted under 35 U.S.C. 154(b) by 1278 days.

(21) Appl. No.: 12/449,944

(22) PCT Filed: Mar. 7, 2008

(86) PCT No.: PCT/PL2008/000020
§ 371 (c)(1),
(2), (4) Date: Jun. 28, 2010

(87) PCT Pub. No.: WO2008/108673
PCT Pub. Date: Sep. 12, 2008

(65) Prior Publication Data
US 2010/0273715 A1    Oct. 28, 2010

(30) Foreign Application Priority Data
Mar. 7, 2007   (PL) .......................................... 381925

(51) Int. Cl.
A61K 38/08    (2006.01)
A61P 25/00    (2006.01)
A61K 38/33    (2006.01)

(52) U.S. Cl.
CPC .............. *A61K 38/08* (2013.01); *A61K 38/33* (2013.01)

(58) Field of Classification Search
CPC .............................. A61K 38/33; A61K 38/08
See application file for complete search history.

(56) References Cited

U.S. PATENT DOCUMENTS 5,919,473 A *    7/1999    Elkhoury ...................... 424/422
2003/0170288 A1*    9/2003    Carr et al. .................... 424/426

FOREIGN PATENT DOCUMENTS

EP    2195006    12/2015

OTHER PUBLICATIONS

Pan, W. Handbook of Biologically Active Peptides, Permeability of the Blood-Brain Barrier to Neurotrophic Peptides, p. 1435, 2006.*
Silbert, B. Enhanced Potency of Receptor-Selective Opioids After Acute Burn Injury, Anesth. Analg. p. 427, 1991.*
Hruby(a) Bioorg. Med. Chem. Let. p. 555, 1998.*
Hruby(b) Bioorg. Med. Chem. Lett. p. 2763, 1999.*
Hruby(c) Life Sciences, p. 1263, 1997.*
Lipkowski(b) Life Sciences p. 1023, 2001.*
International Search Report issued by the International Searching Authority (ISA/EP) on Jan. 10, 2008 in connection with International Application No. PCT/PL2008/000020.
WO 2004/014943 A1 (Lipkowski Andrzej W. et al) Feb. 19, 2004.
WO 2001/24831 A (Shearwater Polymers Inc.) Apr. 12, 2001.
Abbruscato Thomas J. et al., "Brain and spinal cord distribution of biphalin: Correlation with opioid receptor density and mechanism of CNS entry", Journal of Neurochemistry, vol. 69, No. 3, (1997), pp. 1236-1245.
Lipkowski, A. et al., "Biological properties of a new fluorescent biphalin fragment analogue", Life Science, vol. 70, No. 8, (2002), pp. 893-897.

* cited by examiner

*Primary Examiner* — Suzanne Ziska
*Assistant Examiner* — Thurman Wheeler
(74) *Attorney, Agent, or Firm* — Gary J. Gershik; Cooper & Dunham LLP

(57) ABSTRACT

Inflammation caused by disease states such as rheumatism, gout, neurodegeneration and tumours result in the increased effectiveness of the opioid peptide biphalin or its analogues, due likely to the increased permeability of the "blood-brain barrier", due to which it becomes possible to use the opioid peptide to produce a new analgesic for use during inflammation caused by rheumatism, gout, neurodegeneration, post-surgical or post-accidental trauma or tumours.

19 Claims, 2 Drawing Sheets

R₁ = D-Ala lub D-Ser lub D-Thr lub D-Met lub D-Leu lub D-Asn lub D-Gln

R₂ = Phe lub Trp

USE OF A PEPTIDE AND AN ANALGESIC PHARMACEUTICAL AGENT

This application is a §371 national stage of PCT International Application No. PCT/PL2008/000020, filed Mar. 7, 2008, and claims priority of Polish Patent Application No. P.381925, filed Mar. 7, 2007, the contents of all of which are hereby incorporated by reference into this application.

Figure 1:
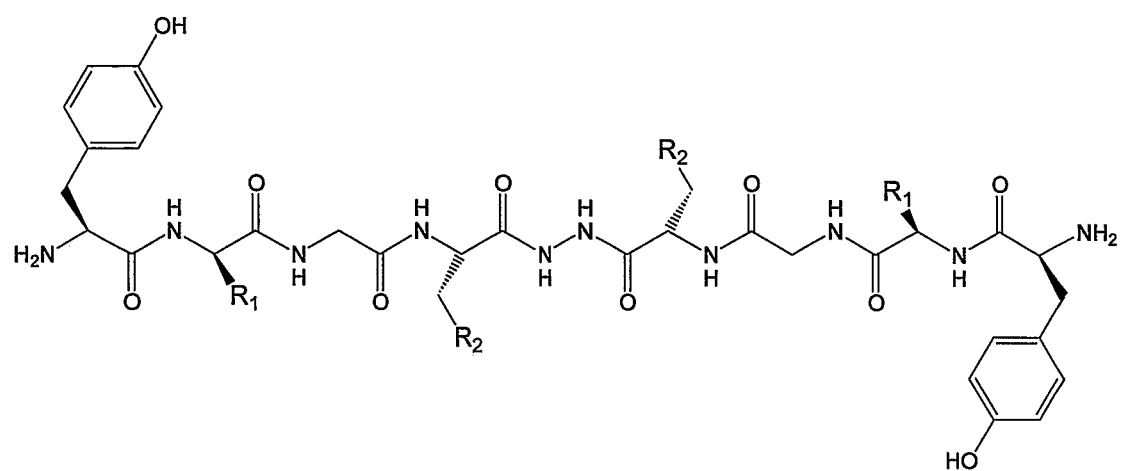
FIG. 1 Chemical structure of an analogue of the opioid peptide, commonly called biphalin.
Figure 2:
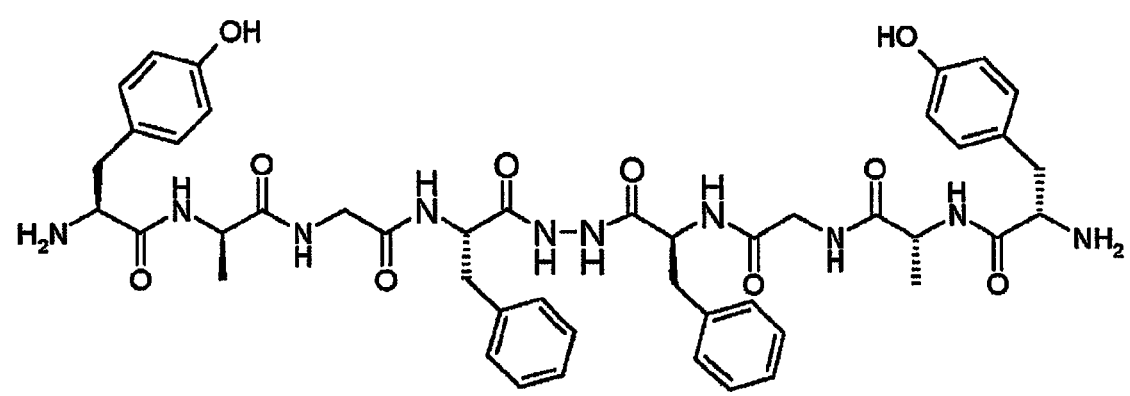
FIG. 2 Chemical structure of the opioid peptide, commonly called biphalin.

The subject of the present invention is the use of an opioid peptide, commonly called biphalin depicted on FIG. 2 or specific analogues thereof, presented in the FIG. 1, particularly in as an intravenous drip or injection or implant, in the treatment of strong, chronic pain caused by inflammation including rheumatoid states, or by neuropathies connected with osteoporosis, or post-accident or post-surgical trauma as well as tumours.

The pain signal induced by organ damage or disease is transmitted to the central nervous system (CNS), where it induces the sensation of pain. The magnitude of the pain stimulus is regulated by the nociceptive and antinociceptive receptors located on neuronal membranes. Endogenous opioid peptides constitute one of the natural factors decreasing the pain signal as a result of activating antinociceptive receptors. These receptors are also activated by the application of analgesic opioid drugs, such as morphine or fentanyl. Unfortunately, the administration of non-peptide analgesics causes a series of adverse reactions, including tolerance and dependency. The application of a peptide analogue of natural opioid peptides, biphalin, makes it possible to decrease tolerance and dependency formation. Unfortunately, research has shown that opioid peptides have a limited ability to pass through the blood-brain barrier. According to animal research data related in 1989 at the International Narcotic Research Conference 1989 and subsequently described in post-conference material by B. S. Silbert, A. W. Lipkowski, D. B. Carr, S. K. Szyfelbein, P. F. Osgood, in "*Peptides as potential nociceptive drugs.*", on pp. 485-488 of "Procc. Int. Narc. Res. Conf. '89", R. Quirion ed., published by Alan R. Liss Inc, New York, 1990, the activity of the opioid peptide presented in FIG. 2 (commonly referred to as biphalin) following intravenous administration is equivalent to that of morphine. Whereas, D. Kosson, I. Maszczynska Bonney, D. B. Carr, E. Mayzner-Zawadzka, A. W. Lipkowski, described this phenomenon in the article entitled Antinociceptive properties of biphalin after intrathecal application in rats: a reevaluation in the Pharmacological Report. Vol. 57, pp. 545-549, 2005, in that bypassing the blood-brain barrier through directly into the subarachnoid space makes it possible for biphaline to exhibit an activity some 1000-fold that of morphine administered the same way. This means that in healthy individuals the blood-brain barrier successfully stops biphalin from penetrating the CNS. The extensive activity of biphalin administered directly into the CNS is the basis of an invention postulating the use of biphalin as a drug for administration using modern local dosage methods, as described in the 2002 patent application P355470, submitted to the Polish Patent Office by A. W. Lipkowski, D. B. Carr, I. Bonney, D. Kosson, A. Misicka-Kesik, entitled "Application of peptides with analgesic properties directly to the site of their predicted analgesic activity". Chronic pain is usually related to a pathological state of inflammation caused by various factors, such as rheumatism or gout or post-surgical or post-traumatic neurodegeneration or tumours. One of the effects of such changes in the organism is an alteration of the permeability of biological barriers, including the barriers separating the blood from the CNS, generally referred to as the "brain-blood barrier". These changes were discussed in the review by W. Pan, entitled "*Permeability of the blood-brain barrier to neurotropic peptides*", on pp. 1435-1442, in the book entitled "Handbook of Biologically Active Peptides", A. J. Kastin Ed., Academic Press, Burlingston, 2006.

The goal of the present invention is to produce an analgesic drug which could be used in patients suffering from chronic pain, at lower doses than corresponding morphine doses. Preferentially, effective treatment doses in ill patients should not induce effects in healthy patients.

During intravenous administration of biphalin and specific analogues thereof in animal models it was unexpectedly noted that disease changes induce increased permeability of the blood-brain barrier, as evidenced by the increased efficacy of peripherally administered peptide.

Unexpectedly, it was shown that the opioid peptide biphalin and some selected analogues thereof have increased activity during pathological inflammation. Due to this, these peptides are an example of a new type of analgesic which, when applied peripherally, is stronger acting when its activity is necessary during pain accompanying a disease state, which results in the decreased efficiency of the blood-brain barrier, particularly due to inflammation.

Thus, the subject of the present invention is the application of a peptide presented in FIG. 1 in the production of an analgesic drug for patients with a weakened blood-brain barrier, wherein the drug production uses a sub-threshold dose.

"Patients with a weakened blood-brain barrier" for the purposes of the present invention are patients suffering disease states, which are known to weaken the blood-brain barrier, meaning an increase in the permeability of the blood-CNS barrier. In particular, these disease states are all disease states accompanied by inflammation. It is commonly known that the blood-brain barrier is weakened in: rheumatoid states, gout, neuropathic and tumour-induced pain. In a preferential embodiment of the present invention, the pain fought can be induced by a tumour, rheumatoid inflammation, gout, multiple sclerosis, osteoporosis, post-surgical or post-accidental trauma and oncogenic changes.

A "sub-threshold dose" for the purposes of the present invention is a dose showing no analgesic activity in healthy persons, meaning persons in whom the blood-brain barrier shows no increased permeability. Because the sub-threshold dose will be different for different species of mammals and patients in various disease states, and will also depend on the method of administration into the bloodstream, it should thus be assumed on a per case basis, that the sub-threshold dose is a dose lower than the lowest effective dose of identically administered morphine capable of eliciting an analgesic effect in said patient. In humans, the minimum effective dose usually used as an initial analgesic dose is 1 mg, as found in literature. Thus, in particular embodiments of the present invention, the sub-threshold dose in humans will be a dose less than 1 mg, preferentially less than 0.1 mg, preferentially less than 0.01 mg, and particularly preferentially, in patients with considerable disease-induced blood-brain-barrier permeability the dose will be less than $10^{-3}$ mg.

The method of administration can be any known method of administration used for morphine. In particular, intravenous administration may be used, particularly as a drip; intraperitoneal or subdermal administration, preferentially as a subdermal intraperitoneal implant.

Also, the preparation administered may be in the form of various formulations. The peptide can be administered as the only active substance, or may be a component of a multi-drug pharmaceutical composition used in therapy. In particular, the peptide used according to present invention can be in the form of a sterile lyophilisate, which is to be dissolved in a certain quantity of physiological saline prior to administration. It may also be used as a ready-to-use solution.

The present invention reveals the use of the opioid peptide with the formula shown in FIG. 1 as an effective analgesic, preferentially following peripheral administration, during disease states which also result in increased blood-brain barrier permeability.

To better illustrate the present invention based on analgesic activity following the peripheral administration of the opioid peptide known as biphalin or its analogues during inflammation inducing changes in blood-CNS barrier permeability including, rheumatoid states, or oncogenic or neuropathic pain, the effects are shown in examples of activity in animal pain research models. However, the scope of present invention should not only be limited to the examples given below.

The similar results and activities shall be obtained for all selected peptides disclosed in the application.

EXAMPLE I

Inflammation was induced in mice through the administration of Freund's adjuvant into a limb. After two days, a progressing inflammation was observed. The analgesic activity of biphalin was observed following a week, during acute pain caused by tail dipping in water at a temperature of 55° C. The intravenous administration of biphalin at 50 µg/kg caused a complete disappearance of the pain reaction in mice with inflammation. In the control group, which lacked the inflammation, no effect was observed for the same dose, administered identically.

EXAMPLE II

In an animal pain model of tumour metastasis, inflammation was induced though the injection of a million human ovarian cancer cells into a rear limb. After two days, we observed a progressing inflammation induced by tumour take. The analgesic activity of biphaline was observed after two weeks, during acute pain caused by tail dipping in water at a temperature of 55° C. The intraperitoneal administration of the opioid peptide biphalin at 100 µg/kg caused a complete disappearance of the pain reaction in mice with inflammation. In the control group, which lacked the inflammation, a similar analgesic effect necessitated the use of a dose of 1 mg/kg.

EXAMPLE III

In an animal pain model of tumour metastasis, inflammation was induced though the injection of a million human ovarian cancer cells into a rear limb. After two days, we observed a progressing inflammation induced by tumour take. The analgesic activity of (Tyr-Ser-Gly-Phe-NH—)$_2$ was observed after two weeks, during acute pain caused by tail dipping in water at a temperature of 55° C. The intraperitoneal administration of the opioid peptide (Tyr-Ser-Gly-Phe-NH—)$_2$ at 50 µg/kg caused a complete disappearance of the pain reaction in mice with inflammation. In the control group, which lacked the inflammation, a similar analgesic effect necessitated the use of a dose of 4 mg/kg.

EXAMPLE IV

In an animal rheumatoid inflammation model, an anaesthetised rat was injected with homogenates of thermically inactivated *Mycobacterium butyricum* suspended in sunflower oil at a volume ratio of 1:1 into the tarsal joint. After two weeks inflammation was observed. The analgesic effect on acute pain was observed using thermal stimulation of the tail. Biphalin administered at 0.5 mg/kg completely blocked pain effects. In the control group given the same amount of biphalin, no antinociceptive effects were observed.

EXAMPLE V

In an animal rheumatoid inflammation model, an anaesthetised rat was injected with homogenates of thermically inactivated *Mycobacterium butyricum* suspended in sunflower oil at a volume ratio of 1:1 into the tarsal joint. After two weeks inflammation was observed. The analgesic effect on acute pain was observed using thermal stimulation of the tail. (Tyr-D-Thr-Gly-Trp-NH—)$_2$ administered at 0.5 mg/kg completely blocked pain effects. In the control group given the same amount of, (Tyr-D-Thr-Gly-Trp-NH—)$_2$ no antinociceptive effects were observed after administration of 4 mg/kg.

The invention claimed is:

1. A method for reducing pain in a patient with a weakened blood-brain barrier, comprising peripherally administering to the patient with a weakened blood-brain barrier a peptide with the formula

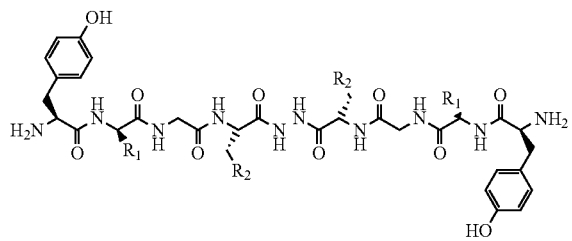

where R1 is an amino acid residue of D-alanine, D-serine, D-threonine, D-methionine, D-leucine, D-asparagine or D-glutamine, whereas R2 is an amino acid residue of phenylalanine or tryptophan thereby reducing pain in the patient with a weakened blood-brain barrier, wherein the peptide is peripherally administered in a sub-threshold dose,
   wherein the sub-threshold dose is a dose which produces no analgesic effect in a patient without a weakened blood-brain barrier, and
   wherein the pain is occurring during disease states accompanied by inflammation.

2. The method of claim wherein the peptide is selected from the group consisting of:

(Tyr-D-Ala-Gly-Phe-NH-)$_2$ (Tyr-D-Ser-Gly-Phe-NH-)$_2$ (Tyr-D-Thr-Gly-Phe-NH-)$_2$

```
(Tyr-D-Met-Gly-Phe-NH-)2

(Tyr-D-Asn-Gly-Phe-NH-)2
```

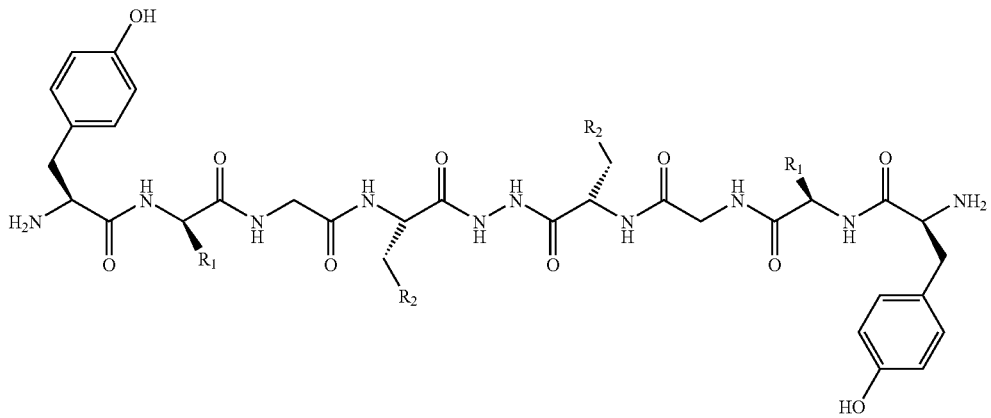

```
-continued (Tyr-D-Leu-Gly-Phe-NH-)2

(Tyr-D-Gln-Gly-Phe-NH-)2

(Tyr-D-Ala-Gly-Trp-NH-)2

(Tyr-D-Ser-Gly-Trp-NH-)2

(Tyr-D-Thr-Gly-Trp-NH-)2

(Tyr-D-Met-Gly-Trp-NH-)2

(Tyr-D-Leu-Gly-Trp-NH-)2

(Tyr-D-Gln-Gly-Trp-NH-)2
or (Tyr-D-Asn-Gly-Phe-NH-)2.
```

3. The method of claim 1, wherein the peptide is biphalin.

4. The method of claim 1, wherein the pain is caused by one of the following diseases: tumours, rheumatoid inflammation, gout, multiple sclerosis, osteoporosis, post-operative or post-accidental trauma or oncogenic changes.

5. The method of claim 1, wherein the peptide is formulated in the form of: a solution, subdermal or intraperitoneal implant.

6. The method of claim 1, wherein the peptide is in the form of a sterile lyophilisate or a solution in a physiological saline solution.

7. The method of claim wherein the peptide is administered intravenously.

8. The method of claim 1, wherein the peptide is administered by intraperitoneal administration.

9. The method of claim 1, wherein the peptide is administered by subdermal administration.

10. The method of claim 1, wherein the sub-threshold dose is less than 1 mg.

11. The method of claim 1, wherein the sub-threshold dose is less than 0.01 mg.

12. The method of claim 1, wherein the sub-threshold dose is less than $10^{-3}$ mg.

13. The method of claim 1, wherein the administration induces an analgesic effect in the central nervous system of the patient with a weakened blood-brain barrier.

14. A method for reducing pain in a patient, comprising peripherally administering to the patient less than 1 mg of a peptide with the formula where R1 is an amino acid residue of D-alanine, D-serine, D-threonine, D-methionine, D-leucine, D-asparagine or D-glutamine, whereas R2 is an amino acid residue of phenylalanine or tryptophan thereby reducing pain in the patient, wherein the pain is occurring during disease states accompanied by inflammation.

15. The method of claim 14, comprising peripherally administering less than 0.01 mg of the peptide.

16. The method of claim 14, comprising peripherally administering less than $10^{-3}$ mg of the peptide.

17. The method of claim 14, wherein the patient has a weakened blood-brain barrier.

18. The method of claim 14, wherein the peptide is selected from the group consisting of:

```
(Tyr-D-Ala-Gly-Phe-NH-)2

(Tyr-D-Ser-Gly-Phe-NH-)2

(Tyr-D-Thr-Gly-Phe-NH-)2

(Tyr-D-Met-Gly-Phe-NH-)2

(Tyr-D-Asn-Gly-Phe-NH-)2

(Tyr-D-Leu-Gly-Phe-NH-)2

(Tyr-D-Gln-Gly-Phe-NH-)2

(Tyr-D-Ala-Gly-Trp-NH-)2

(Tyr-D-Ser-Gly-Trp-NH-)2

(Tyr-D-Thr-Gly-Trp-NH-)2

(Tyr-D-Met-Gly-Trp-NH-)2

(Tyr-D-Leu-Gly-Trp-NH-)2

(Tyr-D-Gln-Gly-Trp-NH-)2
or (Tyr-D-Asn-Gly-Phe-NH-)2.
```

19. The method of claim 14, wherein the peptide is biphalin.

* * * * *